United States Patent [19]

Bode

[11] 4,080,276
[45] Mar. 21, 1978

[54] GAS SENSOR WITH PROTECTIVE COATING AND METHOD OF FORMING SAME

[75] Inventor: James Daniel Bode, Royal Oak, Mich.

[73] Assignee: Bendix Autolite Corporation, Fostoria, Ohio

[21] Appl. No.: 790,799

[22] Filed: Apr. 25, 1977

[51] Int. Cl.² ............................ C23C 3/04; C23D 5/02; G01N 27/46
[52] U.S. Cl. .................................... 204/195 S; 60/276; 123/119 E; 427/126; 427/226; 427/372 A; 427/376 A; 427/376 C
[58] Field of Search ............................ 204/1 S, 195 S; 427/126, 226, 372 A, 372 B, 376 A, 376 C; 60/276; 123/119 E

[56] References Cited

U.S. PATENT DOCUMENTS

| 3,645,875 | 2/1972 | Record et al. | 204/195 S |
| 3,841,987 | 10/1974 | Friese et al. | 204/195 S |
| 3,978,006 | 8/1976 | Topp et al. | 204/195 S X |

FOREIGN PATENT DOCUMENTS

| 2,206,216 | 8/1973 | Germany | 204/195 S |
| 2,341,256 | 2/1975 | Germany | 204/195 S |
| 2,502,409 | 7/1976 | Germany | 204/195 S |

Primary Examiner—G. L. Kaplan
Attorney, Agent, or Firm—William G. Kratz; Raymond J. Eifler

[57] ABSTRACT

A solid electrolyte oxygen sensor has a protective coating to protect a catalyst or conductive film thereon, which coating is formed as an inorganic reaction product of an oxide material and an inorganic acid which forms a matrix to bond the oxide material as an adherent coating over the film.

15 Claims, 2 Drawing Figures

GAS SENSOR WITH PROTECTIVE COATING AND METHOD OF FORMING SAME

BACKGROUND OF THE INVENTION

Gas sensors, such as those used to determine the oxygen content of exhaust from automobile engines, are based on electrochemical cell measurements. Electrodes of such cells are often exposed to high temperatures and fast moving gaseous mixtures and the electrode on the outer surface of the cell suffers rapid deterioration. Mechanical baffles are generally used to reduce the deterioration, but it is often highly desirable to produce additional protection to extend the life of the sensor electrode.

As a protective measure for the outer electrode surface, porous oxide coatings have been proposed to cover the electrode, with such coatings applied by plasma or flame spraying techniques. Such techniques are comparatively expensive, however, and their application subjects the sensor and the electrode being coated to severe temperature shocks and the stress of high velocity, hot gas flow during the application of the coating. Such coatings are described, for example, in U.S. Pat. No. 3,645,875 which discloses application of a thin protective layer of solid refractory material over an electrode film, the protective layer being applied by firing a paste at a temperature of about 1750° C or more, or by flame spraying which also requires high temperature treatment. Also, in U.S. Pat. No. 3,978,006, such a protective coating is disclosed which is formed primarily by brushing on an aqueous suspension of an oxide material and thereafter burning on, or sintering, at temperatures above the expected operating temperature of the sensor. Plasma spray or reactive vaporization which require such high temperatures are also suggested for application of the protective layer.

The present invention is directed to a process for forming a protective coating of oxide material over the electrode of a sensor element which is easier to effect and which does not subject the sensor and electrode to temperature or gas flow stresses or high firing temperatures.

SUMMARY OF THE INVENTION

This invention provides an improved oxygen sensor which has a protective coating of a catalyst film which is formed of an oxide material within a matrix of an inorganic reaction product of an inorganic acid and oxide material or a corresponding hydroxide material.

The invention is an electrode element 10 for sensing oxygen characterized by a body 12 of a solid electrolyte for transferring oxygen ions, the body having an inner surface having conductive means 14 thereon and an outer surface having a conductive means or conductive catalyst film 16, and a porous protective coating over the outer film, which protective coating is a reticular structure comprising discrete particles of an oxide 18 interconnected by a matrix 20 of a salt or other inorganic reaction product of the oxide material. The invention also is characterized by a process for forming such a porous protective coating over a conductive catalyst film on a solid electrolyte base by mixing at least a portion of the oxide material or a corresponding hydroxide material with an inorganic acid which forms an inorganic reaction product therewith, depositing the oxide over the film and heating the oxide material including said portion to a temperature of between 100°–1000° C to form an inorganic reaction product matrix to bond discrete oxide particles as an adherent coating on the film.

DETAILED DESCRIPTION OF THE PREFERRED EMBODIMENT

Figure 1:
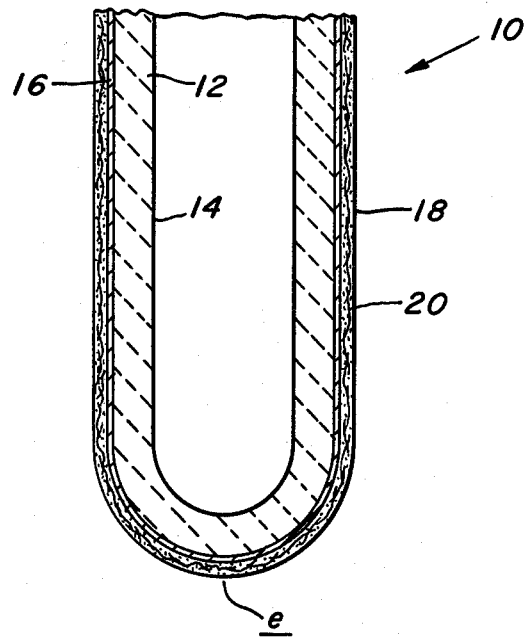
FIG. 1 is a schematic, cross-sectional view of a sensor prepared in accordance with the present invention.
Figure 2:
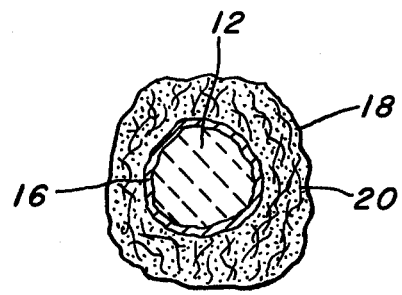
FIG. 2 is an enlarged plan view of a cut-away portion of the exterior surface area of the sensor exposing various layers on the electrolyte body.

Referring now to FIG. 1, there is illustrated an oxygen sensor 10 prepared according to the present invention. The sensor 10 comprises generally a hollow tubular or thimble-like solid electrolyte body 12 for transferring oxygen ions and which is constructed of known oxygen-ion transferring material. The body 12 may be formed from zirconium dioxide, which may contain various stabilizing materials, calcium oxide, yttrium oxide, thorium dioxide, or the like, the body being open at one end and closed at its other end e. Along the inner surface of the body 12 there is provided a conductive means 14 which may be a strip of conductive material or a layer or film of conductive material, such as platinum, and which may be applied to the inner surface in a known manner.

The body 12 has on its outer surface a conductive film 16, usually catalytic, applied thereto. This catalyst film may completely cover the outer surface or may cover a sufficient area to provide a conductive path along the outer surface. This film is usually platinum or a platinum family catalyst and is subject to attrition or wearing in use.

In order to protect the platinum film 16, an outer porous protective coating is provided over the platinum film which is composed of oxide particles 18 which are interconnected by a matrix 20. The oxide particles may comprise aluminum oxide, zirconium dioxide, magnesium zirconate, thorium dioxide, spinel oxides, mullite, an aluminum silicate such as kaolin, or other known protective oxides which provide protection for the catalyst film to reduce attrition and wearing of the catalyst film during exposure to hot gaseous streams in which the sensor is to be used. There may be used in conjunction with the oxide material a portion of the corresponding hydroxide, for example, a mixture of aluminum oxide containing a portion of aluminum hydroxide.

In formation of the electrode elements of the present invention, a body of solid electrolyte has a conductive means applied to the inner surface thereof and a conductive film, preferably a catalyst film such as platinum, applied to the outer surface. The oxide material, or at least a portion thereof, which is to be used in forming the porous protective coating over the film is mixed with an inorganic acid that reacts with the oxide. A hydroxide compound may be added to the mixture to augment the inorganic acid reaction with the oxide. The amount of inorganic acid to be added to the oxide in the mixture is between about 1–20 percent by weight based upon the oxide, with about 3–5 percent being preferred. An especially useful acid is phosphoric acid, while the use of hydrochloric acid, nitric acid, boric acid and silicic acid, are also proposed. The oxide material that is to be mixed with the inorganic acid must be in a reactive form, that is, for example, when aluminum oxide is used, the oxide must be in a chemically reactive form and not "dead burned" such as is used in refractory material.

The oxide material and inorganic acid are formed into a paste or slurry with water or other suitable liquid vehicle and may be applied by brushing, dipping, spraying or other means without subjecting the sensor unit to deleterious stresses. After the application thereof, the coated sensor is dried by heating to about 100° C and, if necessary, the oxide reacted with the inorganic acid by further heating to reaction temperature, but below sintering temperatures for the oxide or catalyst, to form an inorganic reaction product matrix. The term inorganic reaction product is used herein to designate acid salts and other salts formed by reaction of the oxide and inorganic acid, as well as glassy materials formed thereby. Generally, the reaction temperature will be between 100°14 1000° C depending upon the particular oxide material used and the particular inorganic acid.

The present process forms a protective coating over the catalyst film of a gas sensor, the coating being in the form of a reticular structure of discrete oxide particles interconnected and adhered to the catalyst film by a matrix of an inorganic acid reaction product of the oxide material. The strong but porous coating is formed without subjecting the sensor to thermal shocks or high gas flows which have been present in prior coating formations.

I claim:

1. In a process for the formation of an electrode element for sensing oxygen, the electrode element comprising a solid electrolyte body for transferring oxygen ions, the body having an inner surface having conductive means thereon and an outer surface having a conductive film thereon, the improvement comprising:

forming a porous protective coating of an oxide over the film without subjecting the film to sintering temperatures for the coating by mixing at least a portion of the oxide material with an inorganic acid which reacts therewith, depositing the oxide on said outer surface and heating the oxide material including said portion to form an inorganic reaction product matrix to bond discrete oxide material as an adherent coating on the film.

2. In the process for formation of an electrode element for sensing oxygen as defined in claim 1, the improvement wherein said oxide material is selected from the group consisting of aluminum oxide, zirconium dioxide, magnesium zirconate, thorium dioxide, spinel oxides, mullite and kaolin.

3. In the process for formation of an electrode element for sensing oxygen as defined in claim 1, the improvement wherein said inorganic acid is selected from phosphoric acid, hydrochloric acid, nitric acid, boric acid and silicic acid.

4. In the process for formation of an electrode element for sensing oxygen as defined in claim 1, the improvement wherein said conductive film on the outer surface is a conductive catalyst film.

5. In the process for formation of an electrode element for sensing oxygen as defined in claim 1, the improvement wherein said oxide material including said portion is heated to a temperature in the range of 100°–1000° C to form said inorganic reaction product matrix.

6. In the process for formation of an electrode element for sensing oxygen as defined in claim 1, the improvement wherein the total amount of said oxide material is mixed with said inorganic acid.

7. In the process for formation of an electrode element for sensing oxygen as defined in claim 1, the improvement wherein said oxide material contains a portion of the corresponding hydroxide material.

8. In an electrode element for sensing oxygen, the electrode element comprising a solid electrolyte body for transferring oxygen ions, the body having an inner surface with conductive means thereon and an outer surface having a conductive film thereon with a porous protective coating over said film, the improvement wherein said porous protective coating comprises a reticular structure of discrete particles of an oxide interconnected by a matrix comprising an inorganic reaction product of an inorganic acid and the oxide material.

9. In an electrode element for sensing oxygen as defined in claim 8, the improvement wherein said solid electrolyte body is of zirconium dioxide.

10. In an electrode element for sensing oxygen as defined in claim 8, the improvement wherein said conductive film on the outer surface is a conductive catalyst film.

11. In an electrode element for sensing oxygen as defined in claim 8, the improvement wherein said oxide is selected from the group consisting of aluminum oxide, zirconium dioxide, magnesium zirconate, thorium dioxide, spinel oxides, mullite and kaolin.

12. In an electrode element for sensing oxygen as defined in claim 8, the improvement wherein said inorganic reaction product comprises a phosphoric acid salt of an aluminum oxide.

13. In an electrode element for sensing oxygen as defined in claim 8, the improvement wherein said oxide material contains a portion of the corresponding hydroxide material.

14. In an electrode element for sensing oxygen as defined in claim 8, the improvement wherein said inorganic reaction product comprises a hydrochloric acid salt of an aluminum silicate.

15. In an electrode element for sensing oxygen as defined in claim 14, the improvement wherein said aluminum silicate is kaolin.

* * * * *